US009766012B2

(12) United States Patent
McLaren et al.

(10) Patent No.: US 9,766,012 B2
(45) Date of Patent: Sep. 19, 2017

(54) APPARATUS AND METHOD FOR DRYING AND STERILIZING OBJECTS IN A LOAD

(75) Inventors: Jami McLaren, Crystal, MN (US); Steven J. Olson, Mahtomedi, MN (US); Kent Larson, Woodbury, MN (US)

(73) Assignee: Sterilucent, Inc., Minneapolis, MN (US)

( * ) Notice: Subject to any disclaimer, the term of this patent is extended or adjusted under 35 U.S.C. 154(b) by 482 days.

(21) Appl. No.: 13/526,872

(22) Filed: Jun. 19, 2012

(65) Prior Publication Data
US 2012/0297638 A1    Nov. 29, 2012

Related U.S. Application Data

(62) Division of application No. 12/483,055, filed on Jun. 11, 2009, now Pat. No. 8,230,616.

(51) Int. Cl.
*F26B 5/04*    (2006.01)
*A61L 2/20*    (2006.01)
*A61L 2/24*    (2006.01)

(52) U.S. Cl.
CPC ............... *F26B 5/04* (2013.01); *A61L 2/208* (2013.01); *A61L 2/24* (2013.01); *A61L 2202/14* (2013.01)

(58) Field of Classification Search
CPC ... B26B 5/04; A61L 2/208; A61L 2/24; A61L 2202/14
See application file for complete search history.

(56) References Cited

U.S. PATENT DOCUMENTS

| | | |
|---|---|---|
| 4,239,731 A | 12/1980 | Gillis et al. |
| 4,241,010 A | 12/1980 | Baran |
| 4,294,804 A | 10/1981 | Baran |
| 4,457,892 A | 7/1984 | Young |
| 4,687,635 A | 8/1987 | Kaehler et al. |
| 4,952,370 A | 8/1990 | Cummings et al. |
| 4,956,145 A | 9/1990 | Cummings et al. |
| 5,084,239 A | 1/1992 | Moulton et al. |
| 5,173,258 A | 12/1992 | Childers |
| 5,317,896 A | 6/1994 | Sheth et al. |
| 5,445,792 A | 8/1995 | Rickloff et al. |
| 5,482,683 A | 1/1996 | Sheth et al. |
| 5,492,672 A | 2/1996 | Childers et al. |
| 5,527,508 A | 6/1996 | Childers et al. |
| 5,830,409 A | 11/1998 | Childers et al. |
| 5,851,485 A | 12/1998 | Lin et al. |
| 5,872,359 A | 2/1999 | Stewart et al. |
| 6,060,019 A | 5/2000 | Spencer et al. |

(Continued)

OTHER PUBLICATIONS

Sterad 200 510(k) notification pp. 344-345, 354, 375, 405-414, 441-452, 455-466.

*Primary Examiner* — Jessica Yuen
(74) *Attorney, Agent, or Firm* — Nikolai & Mersereau, P.A.; Thomas J. Nikolai

(57) ABSTRACT

The removal of moisture from an object to be sterilized is provided through at least the steps of placing the load in the chamber, reducing the pressure within the chamber to increase the rate of evaporation of moisture from the load, monitoring over a predetermined period of time the increase in the quantity of vapor within the chamber resulting from evaporation of moisture from the load, admitting gas into the chamber and repeating the steps following placing the load into the chamber.

11 Claims, 13 Drawing Sheets

(56) References Cited

U.S. PATENT DOCUMENTS

| | | | |
|---|---|---|---|
| 6,261,518 | B1 | 7/2001 | Caputo et al. |
| 6,365,102 | B1 | 4/2002 | Wu et al. |
| 6,451,254 | B1 | 9/2002 | Wang et al. |
| 6,528,016 | B1 | 3/2003 | Kohler et al. |
| 6,599,471 | B2 | 7/2003 | Jacobs et al. |
| 6,673,313 | B2 | 1/2004 | Wang et al. |
| 6,746,647 | B2 | 6/2004 | Kohler et al. |
| 6,818,178 | B2 | 11/2004 | Kohl et al. |
| 6,893,530 | B2 * | 5/2005 | Kishimoto et al. ........... 156/285 |
| 7,229,591 | B2 | 6/2007 | Wu et al. |
| 2007/0274858 | A1 | 11/2007 | Childers et al. |
| 2008/0011078 | A1 | 1/2008 | Ehrhard et al. |

* cited by examiner

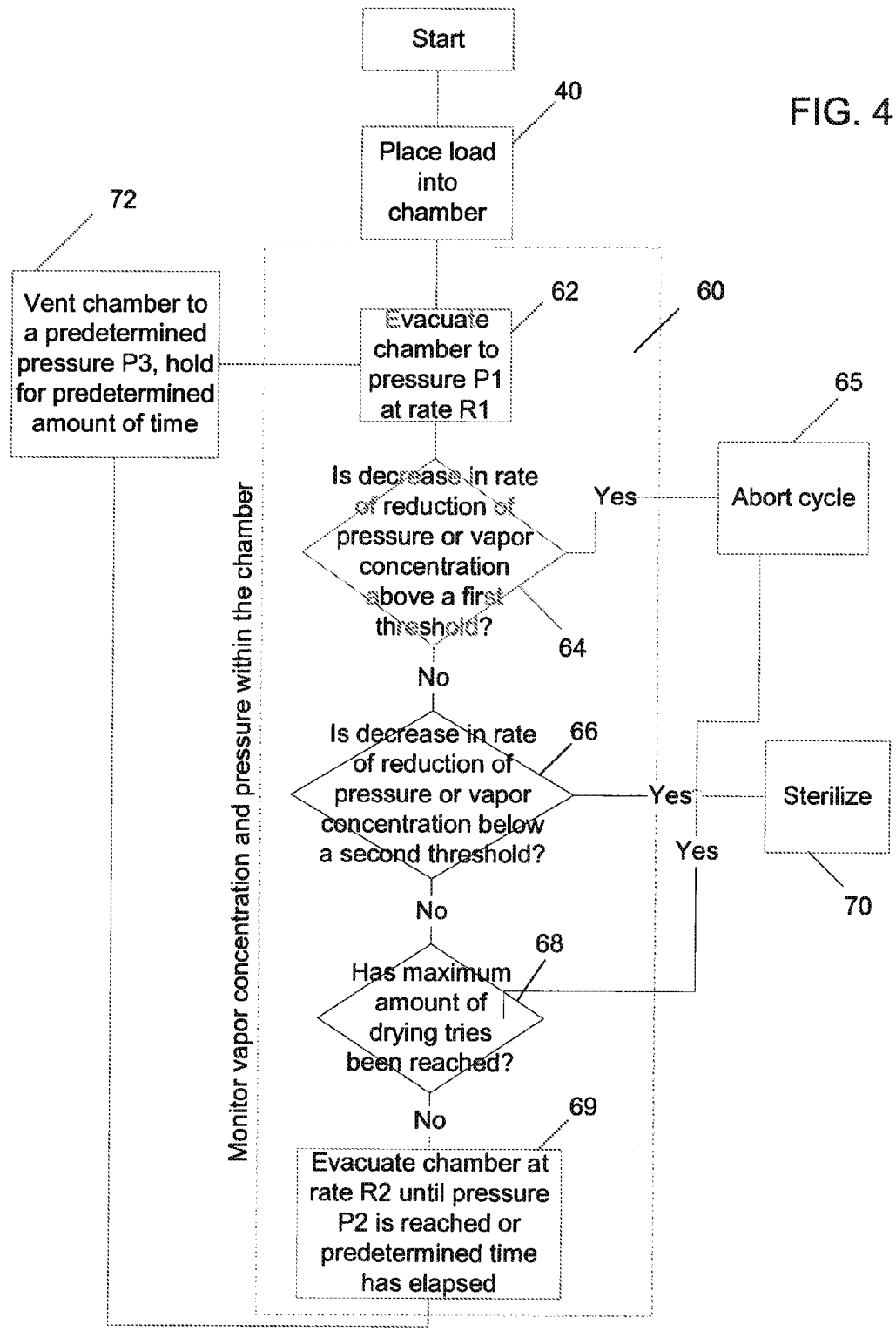

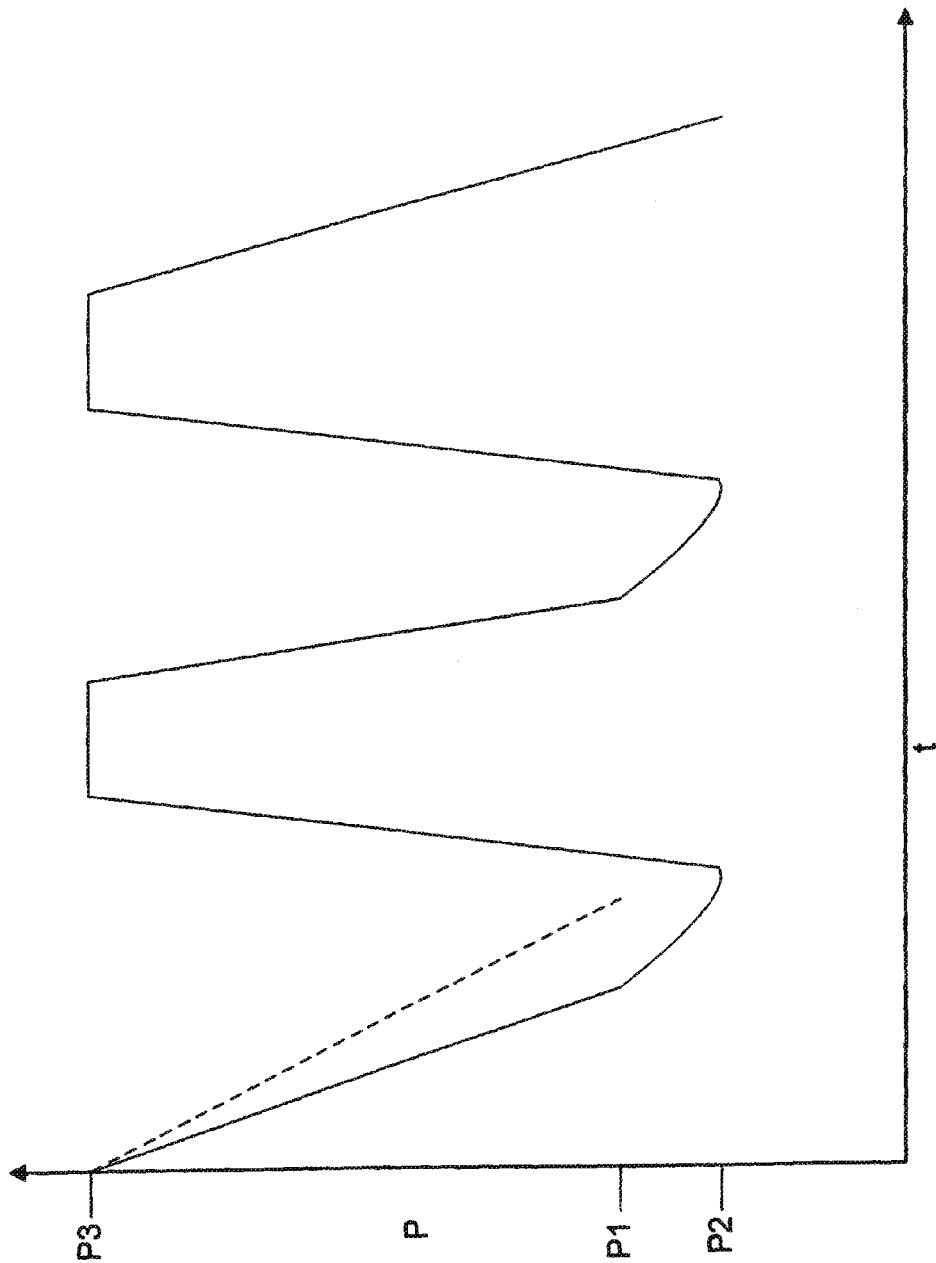

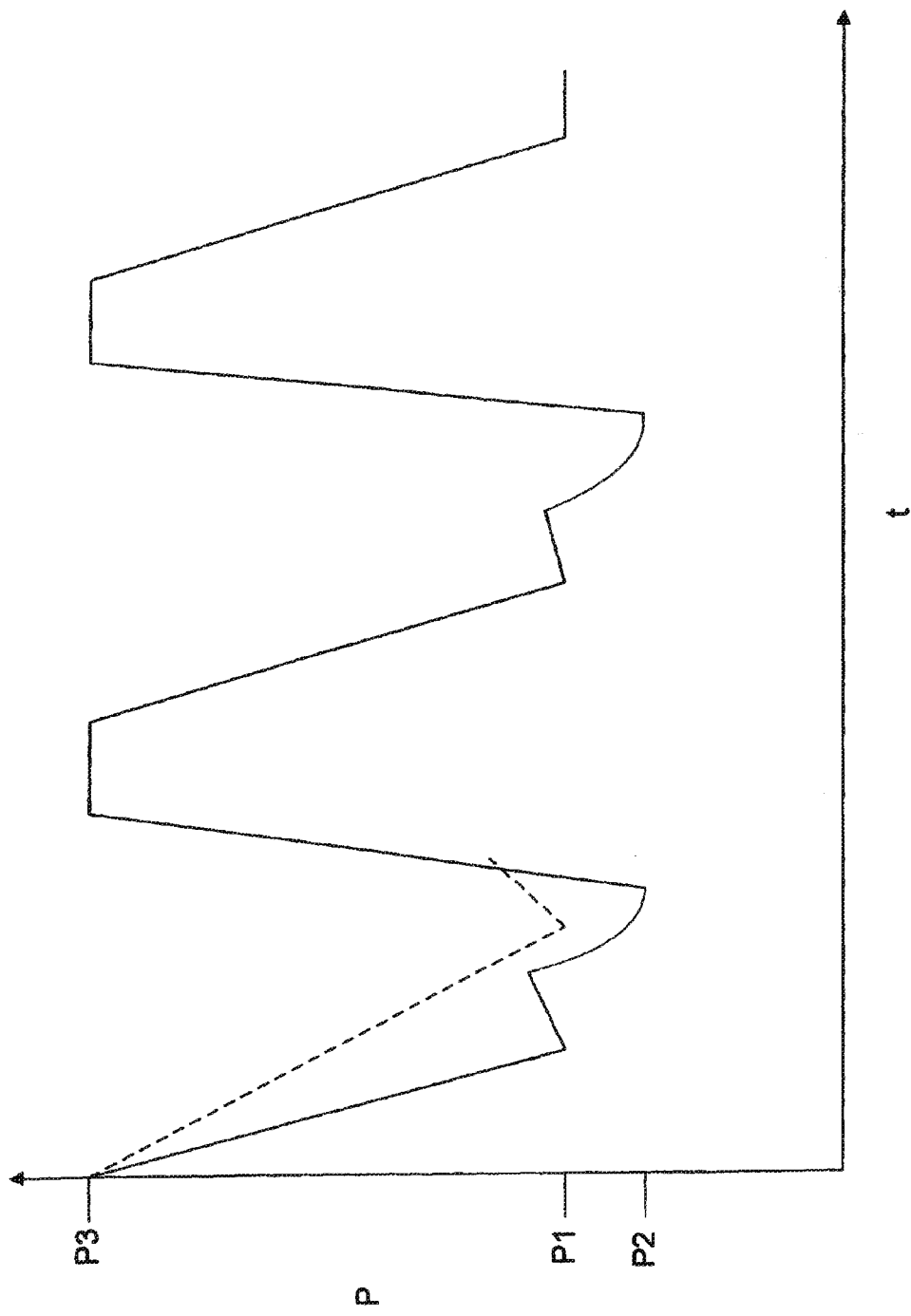

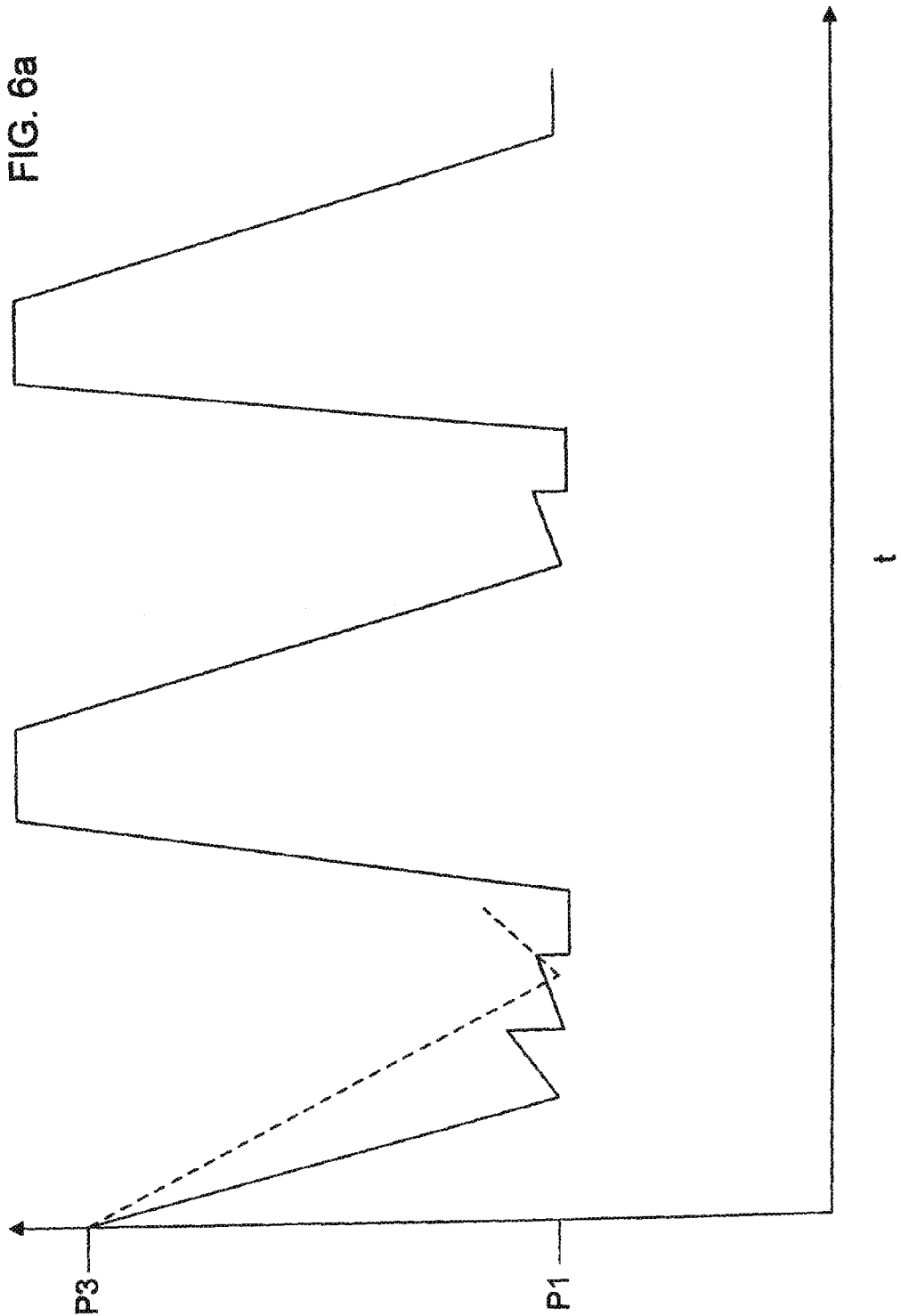

APPARATUS AND METHOD FOR DRYING AND STERILIZING OBJECTS IN A LOAD

CROSS-REFERENCE TO RELATED APPLICATION

This application is a divisional of application Ser. No. 12/483,055, filed Jun. 11, 2009, and entitled "Apparatus and Method for Drying and Sterilizing Objects in a Load".

The U.S. Government has a paid-up license in this invention and the right in limited circumstances to require the patent owner to license others on reasonable terms as provided for by the terms of Contract No. W81XWH-05-1-0398 awarded by USA Medical Research ACQ Activity; Office of Naval Research SBIR Phase II, Contract No. N00014-06-M-0301 and Contract No. 5R44HL074653-03 awarded by National Institute of Health SBIR Phase II.

BACKGROUND OF THE INVENTION

I. Field of the Invention

The present invention relates generally to the removal of moisture and sterilization of loads. More particularly, this invention relates to removing moisture from objects. The invention further relates to vapor sterilization of objects which are sufficiently dry for such sterilization to be effectively and efficiently achieved.

The surfaces of virtually all objects are covered with transmissible agents and undesirable materials such as biological substances (blood, bodily fluids, excrement, etc.), fungi, bacteria and viruses. It is often necessary to pre-treat objects such as food products, packaging, biological materials, medical implements and the like, to initially remove any undesirable materials. Pre-treatment of these objects typically includes washing and cleaning the objects so no visible substances remain on the surfaces. After these objects are washed, they must be dried in a manner where substantially all of the moisture is removed from the surfaces of the object. Most known methods of removing moisture from the object requires a user to hand dry the object or allow warm or hot gases to pass over and around the objects. These methods do not ensure complete removal of moisture from the objects, particularly when the surfaces of the objects include confined, small, difficult to reach spaces.

Moisture on the surfaces of objects can damage the objects, limit their effective life or otherwise limit their use. Likewise, moisture on the surface of an object hinders proper sterilization of the object when certain sterilization processes are used. Therefore, the object should be substantially free of moisture prior to any such sterilization efforts.

Various methods for sterilizing objects are known. Known methods of sterilization include heating and chemical treatments. Heat sterilization involves applying steam or dry heat to the objects to be sterilized for a suitable period of time. While this method of sterilization is effective for many objects, heat sterilization is not suitable for objects adversely affected by heat. Objects subjected to heat sterilization can reach 100° to 120° C., temperatures sufficiently high to cause damage to certain objects. Further, heat sterilization often requires large amounts of electrical power and water. These resources are not always readily available in remote locations such as military field hospital settings.

Chemicals which have been used in the past to sterilize objects include alcohols, aldehydes, phenols, ozone, ethylene oxide, and hydrogen peroxide. Sterilization using chemicals can be accomplished at lower temperatures and can be highly effective when sterilizing heat-sensitive items. However, care must be taken to ensure all surfaces are sterilized. This is a difficult task when sterilizing catheters, tubing, and other objects with small, confined, difficult-to-reach spaces.

Various gases and vapors have been used as a sterilant when sterilizing heat sensitive objects (the words "gas" and "vapor" in their singular and plural form will be used interchangeably hereinafter to refer to generically both gases and vapors). Proper care and handling of such sterilants are crucial because of their potentially toxic nature. Using hydrogen peroxide gas as a sterilant offers certain advantages. First, low concentration aqueous solutions of hydrogen peroxide are generally safe to handle. Second, at low concentrations hydrogen peroxide is non-corrosive and can therefore be stored for long periods of time. Even at higher concentrations, suitable packaging can be employed to protect humans from exposure. When properly packaged, the shelf-life of hydrogen peroxide solutions can be multiple years in length. Third, hydrogen peroxide degrades into water and oxygen, two non-toxic byproducts. Fourth, sterilization using hydrogen peroxide gas as a sterilant can be performed at lower temperatures (such as temperatures less than 60° C.) than heat sterilization. Virtually all products requiring sterilization are not adversely affected by temperatures in this range. Fifth, hydrogen peroxide gas requires less energy and essentially no water when compared to heat sterilization methods. The only water required is the water used to form the solution when aqueous hydrogen peroxide is used as the sterilant source.

When hydrogen peroxide gas is used, it is desirable to ensure the load is sufficiently dry for effective and efficient sterilization. This is particularly important when the load of objects being sterilized includes objects with lumens such as catheters or other objects having confined, hard-to-reach spaces. Also, the concentration of hydrogen peroxide gas or other sterilant in a sterilization chamber should be effectively controlled to ensure proper sterilization. Achieving the most efficient and effective hydrogen peroxide concentration ranges and times for sterilization is dependent on the objects, or load, the environment and other operational factors. For these reasons, it is important to accurately monitor and control the hydrogen peroxide concentration throughout a sterilization process. The same is true when other gas sterilants are employed.

A variety of problems exists with prior art equipment and methods used to dry and sterilize objects. As noted above, they often have significant power and water requirements. These resources are sometimes scarce. They also are often ineffective when there is a need to sterilize the interior of confined areas such as the lumens of medical equipment. Prior art chemical vapor sterilizers have been imprecise and inflexible in the delivery of sterilant leading to several problems. In some cases, the quantity of sterilant and the manner of delivery have been inadequate for effective sterilization. In other cases too much sterilant has been delivered resulting not only in waste, but also in excessively high concentrations of residual sterilant coating the items to be sterilized and interior surfaces of the sterilization chamber. The residual sterilant must be removed or its concentration reduced to safe levels before the sterilized items can safely be used or the sterilization chamber even opened for removal of the articles.

In view of the foregoing, there is a need for improved methods to remove moisture from objects in an effective and efficient manner. Likewise, there is a need for improved methods of delivering a vapor sterilant to the load. These needs are addressed by the present invention.

SUMMARY OF THE INVENTION

To overcome the problems associated with prior art drying systems and prior art sterilization systems, a first object of the present invention is to provide an apparatus capable of drying and/or sterilizing a load having limited power requirements and virtually no water requirements.

Another object of the present invention is to provide such an apparatus capable of being precisely controlled to eliminate moisture from a load, even when the load includes objects having confined, and otherwise difficult-to-dry spaces.

Still another object of the present invention is to provide such an apparatus capable of performing effective and efficient drying at temperatures low enough to prevent damage to heat-sensitive items to be dried.

Another object of the invention is to provide such an apparatus capable of determining the moisture content of a load and aborting the drying process if moisture content is too high for effective and efficient drying using the drying process to be employed.

Another object of the invention is to provide such an apparatus capable of determining when the moisture content of a load is sufficiently dry for sterilization or for some other purpose.

Still another object of the present invention is to provide drying processes used with such an apparatus which meet one or more of the foregoing objectives.

A further object of the invention is to provide an apparatus capable of controlled delivery of sterilant to the interior of a chamber.

A still further object of the invention is to provide an apparatus capable of sensing concentrations of vaporous materials and the pressure in the chamber and regulating the delivery of sterilant based on the sensed concentrations and pressures.

Another object of the invention is to employ processes using such an apparatus ensuring precise delivery of predetermined quantities of sterilant to obtain predetermined concentrations.

Another object of the invention is to provide such an apparatus and process capable of automatically assessing the concentration of sterilant in the chamber, calculating the quantity of additional sterilant required to reach a predetermined level and then controlling the delivery of sterilant into the chamber to reach the predetermined level.

Still another object of the invention is to provide a process employing such an apparatus to provide multiple sterilant diffusion periods at differing yet highly controlled concentration levels to provide effective sterilization and prevent waste of sterilant.

Still another object of the invention is to provide such a sterilization process ensuring thorough sterilization of the surfaces of confined spaces such as the lumens of a device.

Still another object of the invention is to provide a process ensuring residual quantities of sterilant, after sterilization, are limited to or easily reduced to safe levels upon completion of sterilization.

These and other objects are achieved when the various embodiments of the process of the present invention are employed. Further, advantages over prior art methods and devices are achieved even if all of the objects of the invention set forth above are not met. Thus, this listing of objects is provided to highlight some of the desired improvement, but is not intended to be limiting of the scope of the claims set forth below.

One embodiment of the present invention relates to removing moisture from a load to be sterilized in a chamber where the steps of the method comprise: placing the load in the chamber, reducing the pressure within the chamber to increase the rate of evaporation of moisture from the load, monitoring over a predetermined period of time the increase in the quantity of vapor within the chamber resulting from evaporation of moisture from the load, admitting gas into the chamber and repeating the reduction of pressure, monitoring and admitting steps until the load is sufficiently dry. If the load is not sufficiently dry after a predetermined number of cycles have been employed, drying will be halted (aborted).

Another embodiment of the present invention relates to removing moisture from a load to be sterilized in a chamber where the steps of the method comprise: placing the load in the chamber, reducing the pressure within the chamber to increase the rate of evaporation of moisture from the load while monitoring changes in the quantity of vapor within the chamber resulting from evaporation of moisture from the load, admitting gas into the chamber and repeating the steps after the step of placing the load in the chamber until the load is sufficiently dry.

Another embodiment of the present invention relates to removing moisture from a load to be sterilized in a chamber where the steps of the method comprise: placing the load in the chamber, reducing the pressure within the chamber at a first rate to a first predetermined pressure and then reducing the pressure within the chamber at a second slower rate to a second predetermined pressure to increase the rate of evaporation of moisture from the load while monitoring changes in the quantity of vapor within the chamber resulting from evaporation of moisture from the load, admitting gas into the chamber, and repeating the steps after the step of placing the load in the chamber until the load is sufficiently dry.

Another embodiment of the present invention relates to removing moisture from a load to be sterilized in a chamber where the steps of the method comprise: placing the load in the chamber, reducing the pressure within the chamber at a first rate to a first predetermined pressure, monitoring over a predetermined period of time the increase in the quantity of vapor within the chamber resulting from evaporation of moisture from the load, reducing the pressure within the chamber at a second slower rate while monitoring changes in the quantity of vapor within the chamber, admitting gas into the chamber and repeating the steps after the step of placing the load within the chamber until the load is sufficiently dry.

Another embodiment of the present invention relates to a method of removing moisture from a load to be sterilized in a chamber where the steps of the method comprise: placing the load in the chamber, operating an evacuation pump to decrease at a first rate the pressure within the chamber down to at least a first predetermined pressure to cause evaporation of moisture from the load, monitoring increases in the quantity of vapor in the chamber resulting from the evaporation of moisture from the load, reducing the pressure within the chamber at a slower rate down to at least a second predetermined pressure to cause additional evaporation of moisture from the load, admitting gas into the chamber to enhance heat transfer to the load, and repeating the steps after the step of placing the load in the chamber to further dry the load.

Another embodiment of the present invention relates to a method for sterilizing a load in a chamber where the chamber is coupled to at least a pressure sensor, a vapor sensor, a source of gas, an evacuation pump and a sterilant source and where the steps of the method comprise: placing the load in the chamber, operating the evacuation pump to decrease the pressure within the chamber, admitting sterilant into the chamber for a predetermined period of time so that the concentration of sterilant in the chamber is substantially at a first predetermined target level, allowing the sterilant within the chamber to diffuse for a first diffusion period, monitoring the concentration of sterilant in the chamber to determine the quantity of sterilant that must be added to the chamber and to calculate the period of time required to admit that quantity of sterilant into the chamber to raise the concentration to substantially a second predetermined level, admitting additional sterilant into the chamber for the calculated period of time, allowing the sterilant within the chamber to diffuse for a second diffusion period, after the second diffusion period admitting a sufficient quantity of gas to increase the pressure within the chamber, and allowing the gas and the sterilant to diffuse for a third diffusion period.

Another embodiment of the present invention relates to a method for sterilizing a load in a chamber where the chamber is coupled to at least a vapor sensor, a pressure sensor, a source of gas, an evacuation pump, and a sterilant source and where the steps of the method comprise: placing the load in the chamber, operating the evacuation pump to decrease the pressure within the chamber to a first predetermined level, admitting sterilant into the chamber for a predetermined period of time, monitoring the concentration of the sterilant within the chamber to ensure the concentration is at least at a first predetermined level and adding more sterilant if needed to reach the first predetermined level, allowing the sterilant within the chamber to diffuse for a first diffusion period, monitoring the concentration of sterilant in the chamber to determine the quantity of sterilant that must be added to the chamber to raise the concentration to a second predetermined level, admitting additional sterilant into the chamber for a calculated period of time based on the determined quantity of sterilant that must be added to raise the concentration to substantially the second predetermined level, monitoring the concentration of the sterilant within the chamber to ensure the concentration is at least at the second predetermined level and adding more sterilant if needed to reach the second predetermined level, allowing the sterilant within the chamber to diffuse for a second diffusion period, and after the second diffusion period, admitting a sufficient quantity of a gas to increase the pressure to substantially a predetermined value within the chamber and maintaining the chamber at least at the increased pressure for a third diffusion period.

Still other embodiments of the present invention involve using one of the drying methods outlined above in combination with one of the sterilization methods outlined above. The embodiments described above and in the Detailed Description are illustrative. Other embodiments within the scope of the invention may be employed. Therefore, the description of these embodiments is not intended to be limiting in any manner with respect to the scope of the claims set forth below.

BRIEF DESCRIPTION OF THE DRAWINGS

FIG. 4 is a flow chart illustrating another drying method.

FIG. 4a is a graph illustrating example plots of pressure versus time when the drying method of FIG. 4 is employed.

FIG. 5a is a graph illustrating example plots of pressure versus time when the drying method of FIG. 5 is employed.

FIG. 6a is a graph illustrating example plots of pressure versus time when the drying method of FIG. 6 is employed.

DETAILED DESCRIPTION

Figure 1:
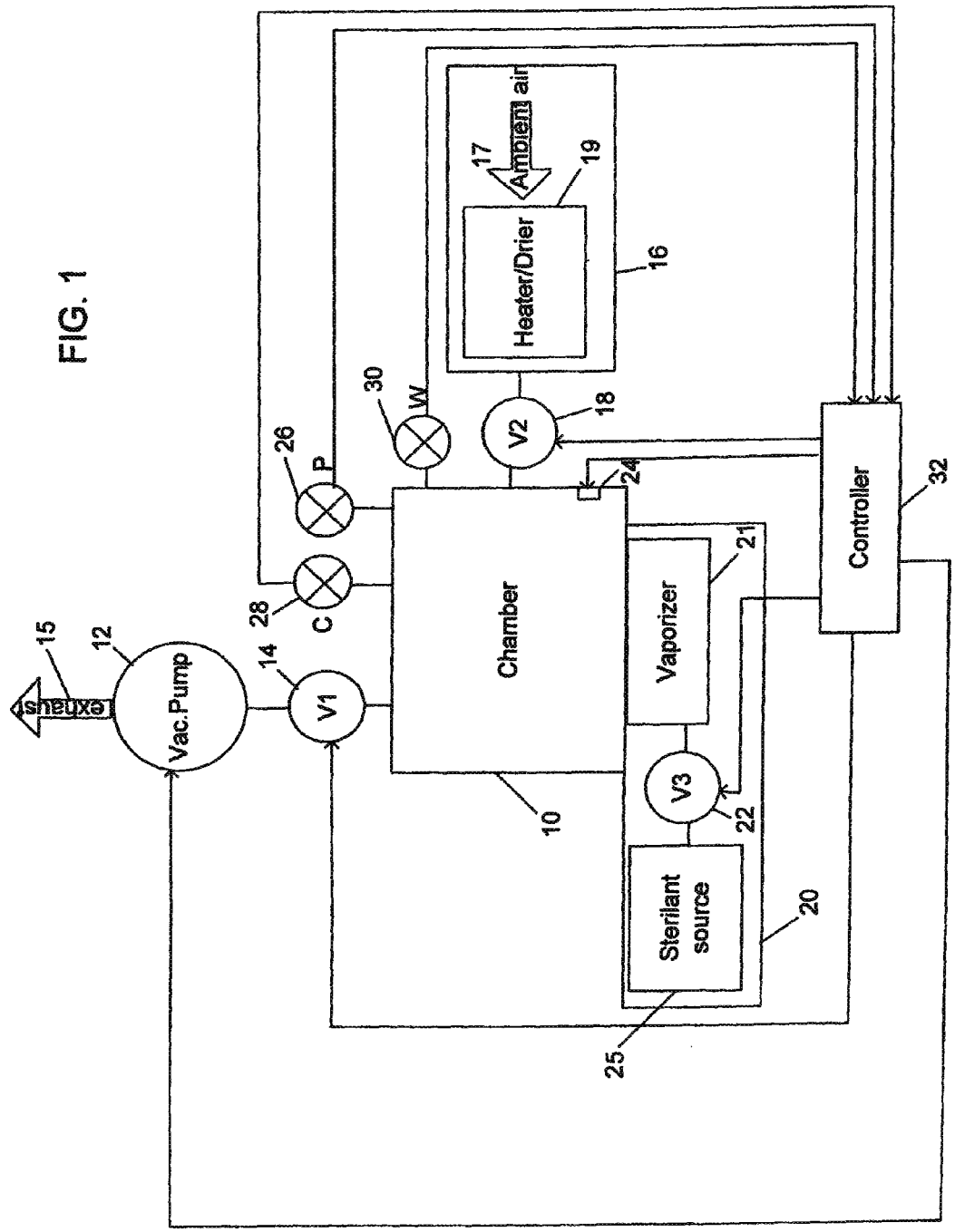
FIG. 1 is a schematic diagram showing the apparatus of the present invention.

A preferred embodiment of the apparatus employed by the present invention is depicted in FIG. 1. As shown, the apparatus comprises a chamber 10. Chamber 10 can be any of a variety of known vacuum or sterilization chambers. Chamber 10 should have an interior large enough to hold items to be treated, and at the same time sufficiently small and light weight, allowing for the chamber to be easily transported. The walls of the chamber 10 should be impermeable to outside elements and should either be made of, or have its interior surface lined with, a material that will not adversely react with materials used in the chamber 10. The chamber 10 should also have an access opening through which items to be treated within the chamber 10 can be inserted and withdrawn. The chamber 10 should also have a sealable door to close and seal the access opening.

An evacuation pump 12 and a first valve 14 are coupled to the chamber 10 to provide the ability to evacuate gases from the chamber 10 and thereby reduce the pressure in the chamber 10 in a controlled fashion. The evacuated gas is exhausted from the chamber 10 as represented by arrow 15. The chamber 10 is also coupled to a source of gas 16 by a second valve 18 and to a source of sterilant 25 by a third valve 22. The source of gas 16 is preferably a source of heated and/or dried air. Thus, the source of gas 16 may simply be ambient air (represented by arrow 17) which may optionally pass through a heater-dryer 19. When employed, the heater-dryer 19 will typically have at least one heating element and a dehumidifying element to condition the air 17 prior to the air 17 entering the chamber 10. Alternatively, the source of gas 16 can be a container in which a drying gas is stored. The source of sterilant 20 can be a container which holds a sterilant gas source and valve. Alternatively and as shown, the source of sterilant 20 can be a container 25 which holds a liquid solution containing the sterilant and a vaporizer 21 which operates in conjunction with a valve 22 to provide controlled delivery of sterilant in a gaseous or vaporous form to the chamber 10, for example through an atomizer or aerosols. It is also contemplated that the sterilant used can be a solid which is either placed directly in the chamber or in the sterilant source. In either manner, the solid would decompose through, for example, melting, dissolving or sublimation, so that sterilant enters the chamber 10.

A gas plasma generator 24 is also provided. If it is desired, the gas plasma generator 24 creates DC gas plasma within the chamber 10. In FIG. 1, the anode of the plasma generator works in conjunction with the walls of the chamber 10 which serve as the cathode. Further information related to plasma generation is disclosed in U.S. Pat. No. 6,113,851 to Soloshenko et al which is incorporated by reference.

The apparatus of the present invention also includes several sensors such as a pressure sensor 26 used to monitor the pressure within the interior of the chamber 10 and one or more vapor concentration sensors 28 and 30. When the sterilant used is hydrogen peroxide and stored as an aqueous solution in container 25, the vapor concentration sensor 28 is preferably used to monitor the concentration of hydrogen peroxide vapor within the chamber 10 and vapor concentration sensor 30 is preferably used to monitor the concentration of water vapor within the chamber 10. Sensors of the type suitable for use as sensors 28 and 30 are disclosed in U.S. patent application Ser. No. 12/231,211 filed Aug. 29, 2008 which is incorporated herein by reference.

Vapor concentration sensor 28, for example, may be a sensor array which may include at least a light source which directs light of a known intensity and of a wavelength range which includes at least a wavelength that is known to be absorbed by hydrogen peroxide through at least a portion of the interior of the chamber 10 to a detector which measures the intensity of light reaching the detector. Similarly, the vapor concentration sensor 30 may be a sensor array comprising a light source which directs light of a known or measured intensity and of a wavelength range which includes wavelengths known to be absorbed by water vapor through at least a portion of the interior of the chamber 10 to a detector which measures the intensity of light reaching the detector.

For even greater precision, the sensors 28 or 30 may include at least an array which has a light source, a splitter and two detectors. The light source generates light having a wavelength range including wavelengths known to be absorbed by a material, the concentration of which is to be measured. The splitter divides the light sending it along two separate paths. It is preferred for the first path to pass through a portion of the interior of the chamber 10 before reaching the first detector. It is preferred for the second path to transmit the light to the second detector without passing through the interior of the chamber 10 and acts as a reference detector measuring the intensity of the light generated by the light source. The signals from the two detectors are used to measure the concentration or quantity of a material (e.g., water vapor or hydrogen peroxide) in the chamber while accounting for changes in intensity of the light generated by the light source.

Sensor arrays similar to those discussed above can be used to measure the concentration of other materials within the chamber 10. Such materials may include other sterilants or the degradation products of the sterilant used. This is achieved by selecting light sources and detectors operating at wavelength ranges known to be absorbed by the specific material, the concentration of which is to be determined.

When selecting the light sources and detectors used in the sensors 28 and 30, operating wavelength ranges should be selected to include wavelengths known to be absorbed by the specific material of interest, but not other materials likely to be present in the chamber. For example, the operating wavelength ranges of the water vapor concentration sensor 30 should include wavelengths known to be absorbed by water vapor, but not hydrogen peroxide. Likewise, the operating wavelength ranges of the hydrogen peroxide vapor concentration sensor 28 should include wavelengths known to be absorbed by hydrogen peroxide, but not water vapor. When other sterilants are employed, the operating wavelength range should be chosen to include wavelengths absorbed by the sterilant, but not the sterilant's degradation products. Alternatively, the selected sensor can have an operating wavelength range including wavelengths known to be absorbed by a degradation product, but not the sterilant itself if the concentration of the degradation product is important.

A controller 32 is also provided. Various general purpose microprocessor-based controllers can be employed as the controller 32. Such controllers typically include not only a microprocessor, but also a clock, memory, and input/output ports. In the present invention, the sensors 26, 28 and 30 are coupled to input/output ports of the controller 32 and supply signals to the controller 32 indicative of pressures and concentrations within the interior of the chamber 10. Other input/output ports of the controller are used to couple the valves 14, 18 and 22, the DC plasma generator 24, the pump 12, the vaporizer 21 and the heater-dryer 19 to the controller 32 so the controller 32 can control such equipment and the drying and sterilization processes employed as well as the temperature of the chamber 10 by controlling heaters built into the walls of the chamber 10. The controller 32 does so in response to signals it receives from an operator interface (not shown) and signals received from the sensors 26, 28 and 30 in accordance with a programmed set of instructions stored in the memory of controller 32. Those skilled in the art will recognize that other sensors can provide signals to the controller (e.g., valve position sensors) without deviating from the present invention. Likewise, as shown in copending U.S. patent application Ser. No. 12/231,211, the concentration sensors may each include a plurality of detectors each of which each send signals to the controller 32 and are used by the controller 32 to accurately determine the concentration of water vapor and sterilant vapor within the interior of the chamber 10.

The programmed set of instructions used by the controller 32 typically includes various routines and subroutines. Some routines control drying of the items placed into the chamber 10. Other routines control sterilization of the items placed in the chamber 10. Still others control removal of residual sterilant from such items and the chamber itself upon completion of sterilization. Examples of routines used for drying and sterilization are discussed below with reference to the drawings.

Figure 2:
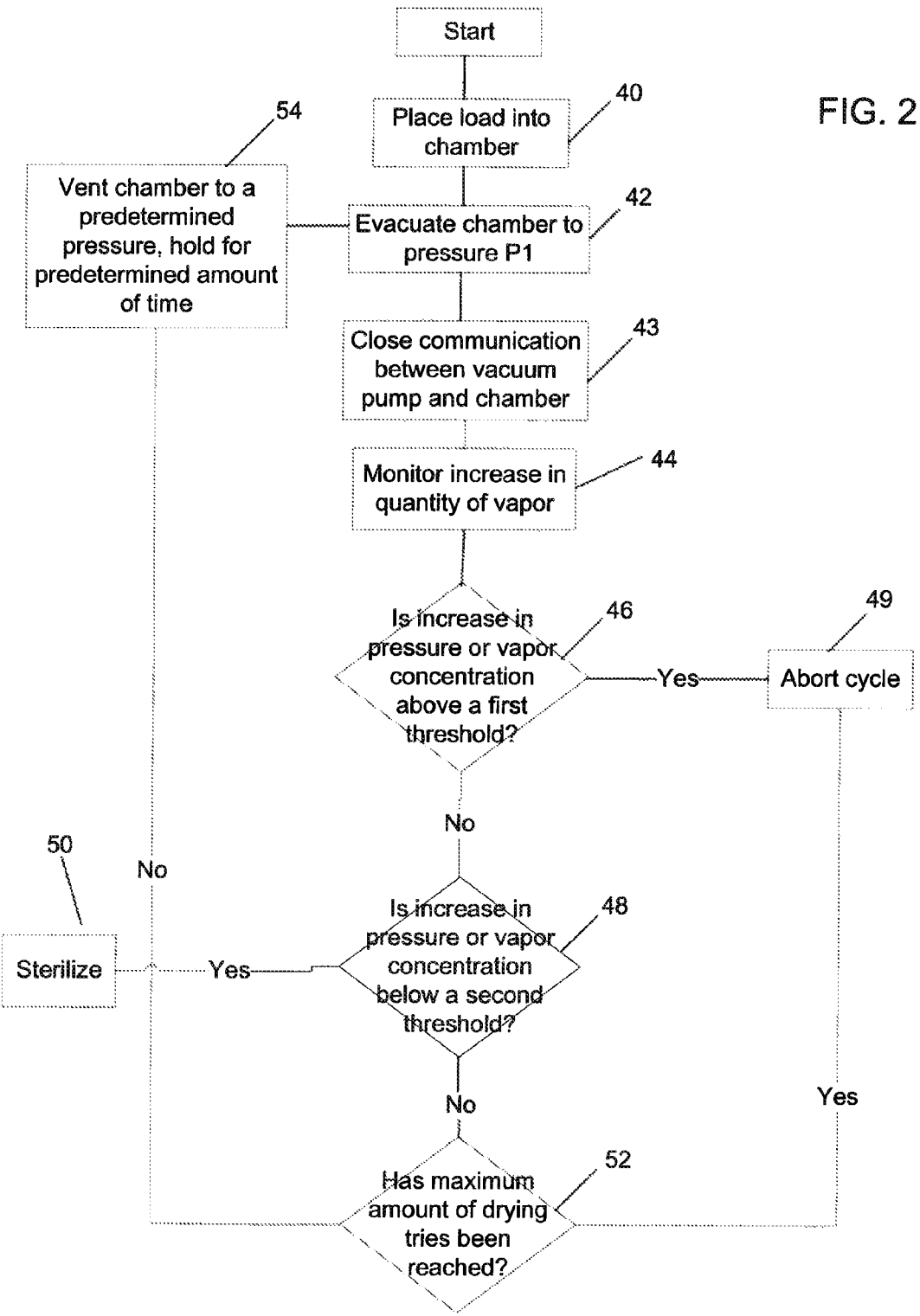
FIG. 2 is a flow chart of a first preferred drying method.

FIG. 2 is a flow chart representing a first method of drying or removing moisture from a load. Prior to initiating the process shown in FIG. 2, the load should have been pretreated to initially clean and dry the load. The process of FIG. 2 commences with step 40 by placing the load within the chamber 10 and closing the chamber's door to seal the access opening. At step 42, the controller closes the valves 18 and 22, if the valves are open, opens the valve 14 and activates operation of the evacuation pump 12 to decrease the pressure within the chamber to a first predetermined subatmospheric pressure P1. Ideally, the pressure P1 will be below the vapor pressure of water at the temperature of the load. The sensor 26 is used to determine when the pressure within the chamber 10 has reached the first predetermined pressure P1. When the pressure P1 is reached within the chamber 10, the controller 32 closes valve 14 at step 43.

At step 44, the controller 32 monitors the signals received from sensor 28 (or alternatively sensor 26) for a predetermined period of time. After the predetermined amount of time has passed, generally between 100 milliseconds and 10 minutes, (and preferably between 20 and 120 seconds), the controller 32 performs step 46 to determine if the increase in vapor within the chamber 10 due to evaporation of moisture from the load, is above a predetermined first threshold. If so, the load is too wet to be dried efficiently using the process of FIG. 2. Thus, if the increase in vapor concentration is above the first threshold the process proceeds to step 49 and the process is aborted (halted)). Sensor 30 provides a direct measure of water vapor concentration changes due to evaporation. Increases in concentration will also increase the pressure within the chamber 10. Thus, the controller 32 can also use the signals from the pressure sensor 26 to determine if the increase in concentration is above the first threshold. If the controller determines the increase in vapor concentration is not above a first predetermined threshold, step 48 is performed by the controller 32. Specifically, the controller 32 will determine if the increase in the quantity of vapor is below a second threshold. The second threshold is indicative of the load being sufficiently dry for sterilization. The second threshold should preferably be in the range of 0 to 0.4 mg/L/s. If, at step 48, the controller 32 determines the increase in vapor concentration is also below the second threshold, the load is deemed to be sufficiently dry and the controller 32 commences sterilization (or an alternative process) at step 50. The various substeps associated with sterilization are described below. At this point, it is important to understand that the method depicted in FIG. 2 is intended to be used both to dry the load sufficiently for sterilization (or some other purpose) and to ensure the load is sufficiently dry for the intended purpose.

If at step 48 the controller 32 determines the increase in vapor concentration is above the second threshold but below the first threshold, step 52 is performed and the controller 32 determines whether a maximum number of drying cycles have been undertaken. If so, step 49 is performed and the process is aborted. If not, the controller 32 performs step 54. When performing step 54, the controller 32 opens the valve 18 to vent the chamber 10 to a predetermined pressure and to expose the load to a gas for a predetermined period of time. Preferably the chamber 10 is vented to approximately atmospheric pressure.

The gas admitted into the chamber 10 at step 54 is preferably a warm, dry gas. The temperature should be high enough to ensure or enhance evaporation of moisture from the load and low enough to prevent damage to the items being sterilized. Likewise, the gas should be sufficiently dry so that it does not add significant moisture to the load and interior of the chamber. When the gas is air the heater-dryer 19, through which the air passes, pretreats the air to achieve a suitable temperature and humidity. While the heater-dryer 19 is available for use, it need not be used if the ambient conditions (i.e., temperature and/or humidity) warrant non-use. After step 54 the controller 32 operates to repeat steps 42-52. These steps are repeated at least one time until either at step 48 the increase in pressure or vapor concentration is below the second threshold so sterilization can begin, or at step 52 the controller 32 determines the maximum number of drying tries has occurred, in which case drying is aborted.

Figure 2A:
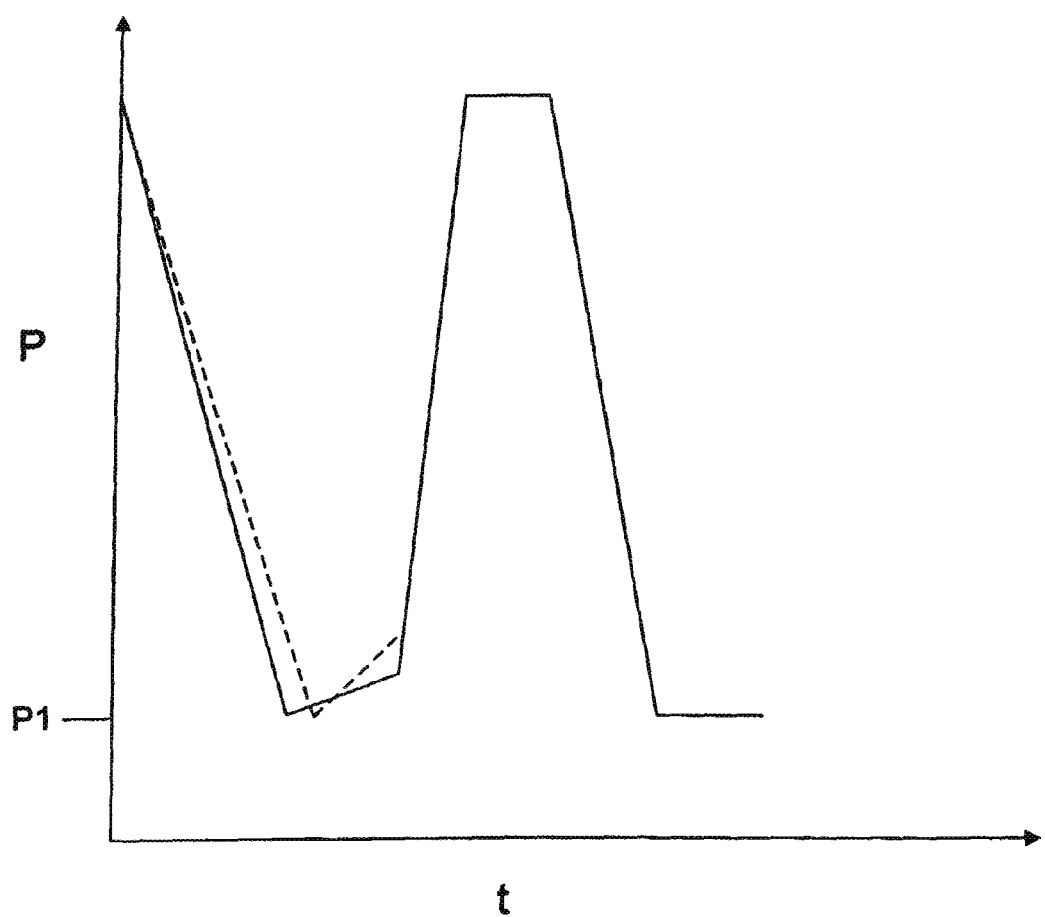
FIG. 2a is a graph illustrating example plots of pressure versus time when the drying method of FIG. 2 is employed.

FIG. 2a represents a plot of pressure versus time when the method of FIG. 2 is employed. The dotted line in FIG. 2a represents graphically what may happen if the load is too wet to be dried or sterilized effectively and efficiently. The reader should appreciate that the dotted line in this graph and the other graphs presented in the figures are intended to reflect examples of the methods and may shift depending upon the degree to which excessive moisture is present. The solid line represents what will happen if the load is initially sufficiently dry to be dried further for sterilization and after two cycles of steps 42-52 is sufficiently dry for sterilization.

Figure 3:
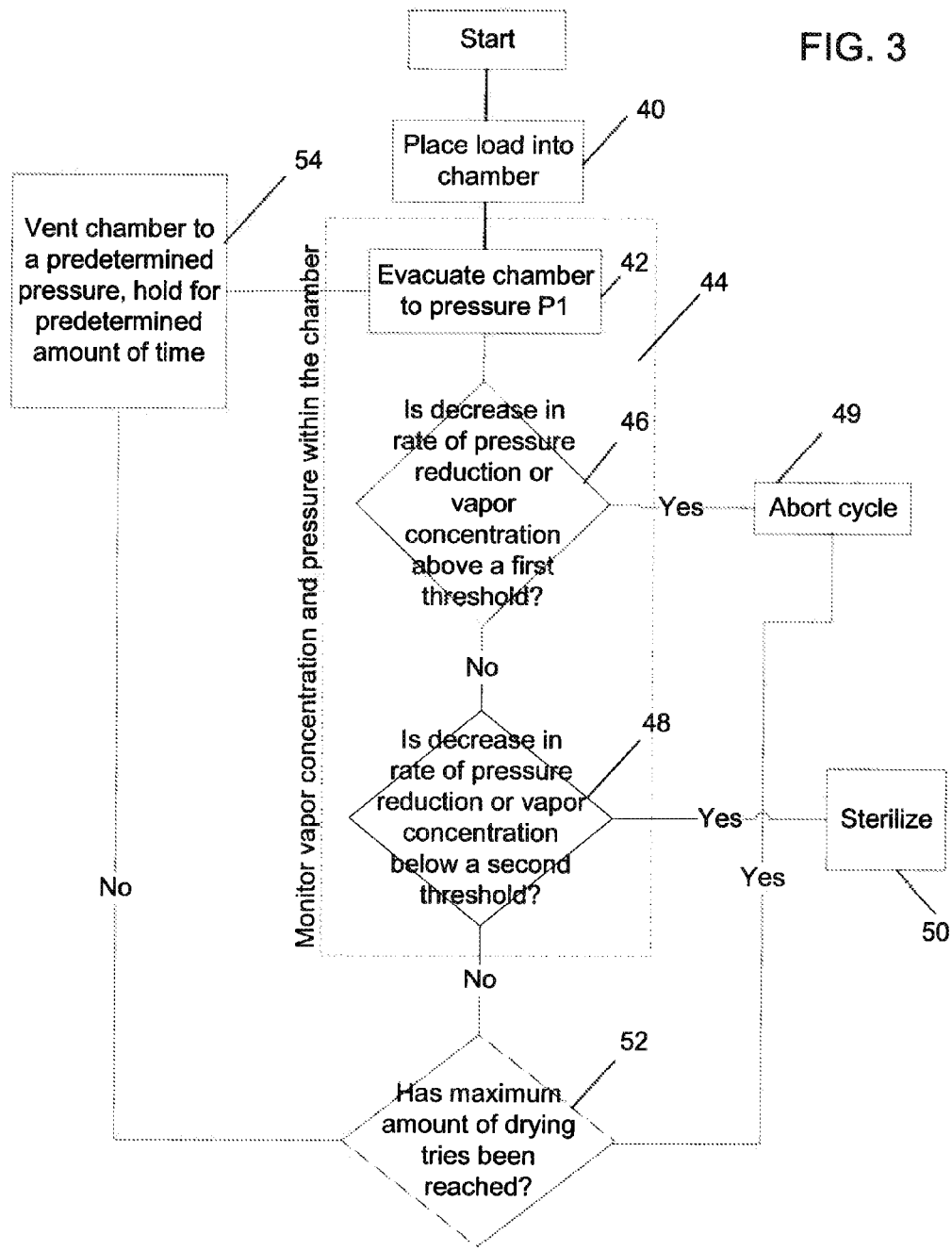
FIG. 3 is a flow chart illustrating a second preferred drying method.

FIG. 3 is a flow chart representing a second method for removing moisture from a load. The method depicted in FIG. 3 is similar to the method depicted in FIG. 2. The method of FIG. 3 differs from the method of FIG. 2 in that the step 44 occurs simultaneously with steps 42-48 rather than separately. In the method of FIG. 3, the change in the vapor concentration within the chamber is constantly monitored throughout steps 42-48. Likewise, the controller 32 can repeatedly perform steps 46 and 48 as the pressure is reduced to P1 rather than only when the pressure reaches P1 as was the case in the method of FIG. 2.

Figure 3A:
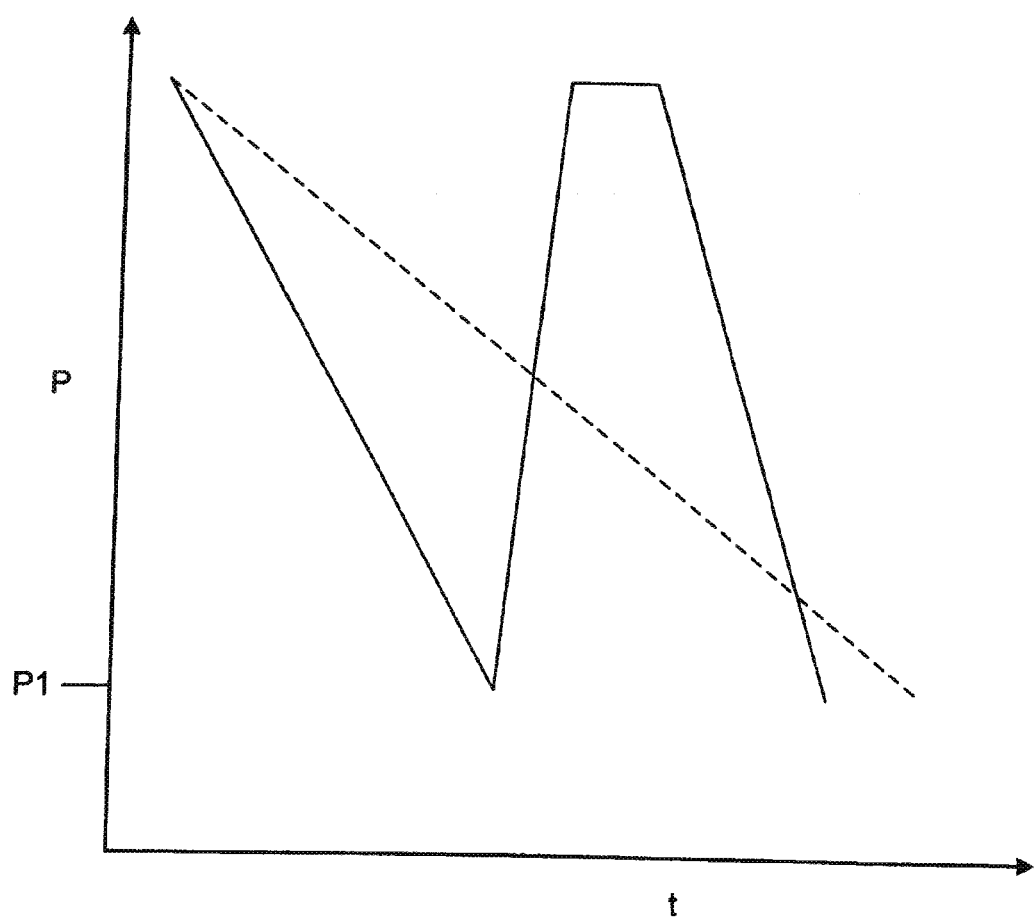
FIG. 3a is a graph illustrating example plots of pressure versus time when the drying process of FIG. 3 is employed.

FIG. 3a is a plot of pressure versus time when the method of FIG. 3 is carried out. The dotted line represents an example where the load is too wet to dry effectively and efficiently. The dotted line stops when the drying process is aborted at step 49. The solid line represents changes in pressure over time when two cycles are needed to sufficiently dry the load for sterilization. While an immediate transition between increasing and decreasing pressures can be employed, the peak pressures can be held for a predetermined period of time, typically less than ten minutes as shown in FIG. 3a.

FIG. 4 depicts another drying method which can be employed using the apparatus of the present invention. Like the methods shown in FIGS. 2 and 3, the drying method of FIG. 4 begins by placing the load in the chamber and then sealing the chamber at step 40. Next, at step 60, the controller 32 monitors both of the sensors 26 and 30 to track changes in water vapor concentration and pressure in the chamber 10 while a number of other steps are carried out by the controller 32. At step 62, the controller 32 ensures the valves 18 and 22 are closed, opens the valve 14 and operates the pump 12 to evacuate the chamber 10 to a first predetermined pressure P1 at a predefined rate R1. Either while the chamber 10 is being evacuated to a pressure P1 or once the chamber 10 has reached that pressure, the controller 32 checks to see if the decrease in the rate of reduction of water vapor has exceeded a first predetermined threshold at step 64. The controller 32 can do so either from signals from the water vapor concentration sensor 30 or based on signals received from the pressure sensor 26. If so, the process is aborted at step 65 because the load is too wet for effective drying. If not, the controller 32 checks to see if the decrease in the rate of reduction of the water vapor is below a second threshold at step 66. Those skilled in the art will appreciate an increase in water vapor also constitutes a decrease in the rate of reduction of water vapor.

If at step 66 the controller 32 determines the increase in water vapor caused by evaporation from the load is below the second threshold, the controller 32 proceeds to step 70 and sterilizes the load. If, however, the controller 32 determines the concentration increase is still above the second threshold, the controller 32 performs step 68 to determine if a maximum number of drying cycles have been performed. If so, drying is aborted (step 65). If not, step 69 is performed.

During step 69, the controller 32 opens the valve 14 and operates the pump 12 to further evacuate the chamber 10 at a second, slower rate R2 until either a lower pressure P2 is reached or a predetermined time has elapsed. The rate R2 is slower than the first rate R1 to prevent ice from forming in the chamber 10. The slower rate R2 also allows for the load to be exposed to pressures where moisture removal is enhanced for longer periods of time. Once pressure P2 is reached it can be held for a predetermined period of time. Evacuating to pressure P2 at a slower pump speed providing rate R2 and then maintaining the pressure P2 for a predetermined period of time is preferable to evacuating to a lower pressure at higher speeds because slower evacuation to higher pressures inhibit the formation of ice due to excessive evaporation of water.

Upon completion of step 69, the controller 32 carries out step 72. Specifically, the valve 18 is opened to vent the chamber 10. The controller 32 closes the valve 18 when the pressure signals from the pressure sensor 26 indicate the pressure within the chamber 10 has reached a third predetermined pressure P3. The chamber 10 can be held at the third predetermined pressure P3 for a predetermined period of time as suggested in the graph of FIG. 4a to enhance heat transfer or the controller 32 can proceed immediately with a repetition of steps 60 through 72. Venting the chamber 10 not only increases chamber pressure, but also heats the load, replacing energy lost due to evaporation of moisture during the drying process. The reader should understand in carrying out the process of FIG. 4, the controller 32 repeatedly performs steps 62 through 72 while step 60 is performed until drying is sufficient for sterilization or the maximum number of drying attempts is reached in which case drying is aborted (step 65).

FIG. 4a represents a plot of pressure versus time assuming two drying cycles. The dotted line represents a condition where the load is too wet to be dried. The solid line represents a condition where the load is successfully and adequately dried by the second cycle. As shown, the pressure decrease becomes more steep as the load becomes more dry.

Still another drying process will now be described with reference to FIG. 5. The process of FIG. 5 again begins at step 40 by placing a load in the chamber 10 and sealing the door. Like in the process of FIG. 4 a number of steps are carried out while step 60 is performed.

Step 60 involves monitoring the concentration and pressure within the chamber using the sensors 30 and 26 respectively.

At step 62 the controller makes sure the valves 18 and 22 are closed, opens the valve 14 and operates the pump 12 to evacuate the chamber 10 to a first pressure P1 at a first rate R1. The pressure P1 is preferably below the vapor pressure of water at the temperature of the load. The first rate (pump speed) R1 is preferably the full operating speed of the vacuum pump 12 and a second, slower rate R2 is a pump speed less than R1. The slower rate R2 is chosen from a range which inhibits formation of ice inside the chamber. Once the pressure reaches the first pressure P1, step 63 is performed and the controller 32 closes the valve 14. At step 64, the controller 32 checks to see if there is an increase in pressure or vapor concentration above a first threshold. The controller 32 does so by checking signals generated by the pressure sensor 26 and/or the water vapor sensor 30. Since the chamber 10 is sealed, any such changes in pressure or concentration are due most likely to evaporation of moisture from the load. With proper maintenance of the chamber 10, it can be assumed that this is the case.

If the increase in pressure or concentration is above the first threshold, the controller 32 aborts the process at step 65. If, on the other hand, the increase in pressure or vapor concentration is below the first threshold as measured during step 64, the controller 32 next determines at step 66 whether the increase in pressure or concentration is also below a second threshold. The second threshold will preferably be in the range of 0.25 to 0.5 mg of water vapor per liter of chamber volume per minute, or a corresponding increase in pressure. If so, the controller 32 proceeds immediately to sterilization step 70. If not, the controller 32 proceeds to step 67.

At step 67, the controller 32 checks to see if a predetermined maximum number of cycles have been performed. If so, drying is aborted at step 65. If not, step 69 is performed.

During step 69, the chamber 10 is evacuated at a slower rate R2 by opening the valve 14 and the operating pump 12 until either a second pressure P2 is reached or a predetermined time has elapsed. Alternatively, once pressure P2 is reached, pressure P2 can be maintained for a predetermined period of time. The slower rate R2 and pressure P2 are chosen from a range which inhibits formation of ice inside the chamber 10. The second pressure P2 will typically be between 5 and 20 Torr. Once step 69 is completed, the controller 32 performs step 71 by opening the valve 18 to vent the chamber 10 to a third predetermined pressure P3 and then closing the valve 18 to again seal the chamber 10 at the third pressure P3 for a predetermined amount of time. The third pressure P3 can be atmospheric pressure or a selected subatmospheric pressure. Steps 60-71 are repeated until either (a) an abort occurs at step 64 if the load is too wet; (b) an abort occurs at step 67 if the maximum number of cycles has been reached; or (c) the load is determined at step 66 to be sufficiently dry for sterilization to take place.

Figure 5:
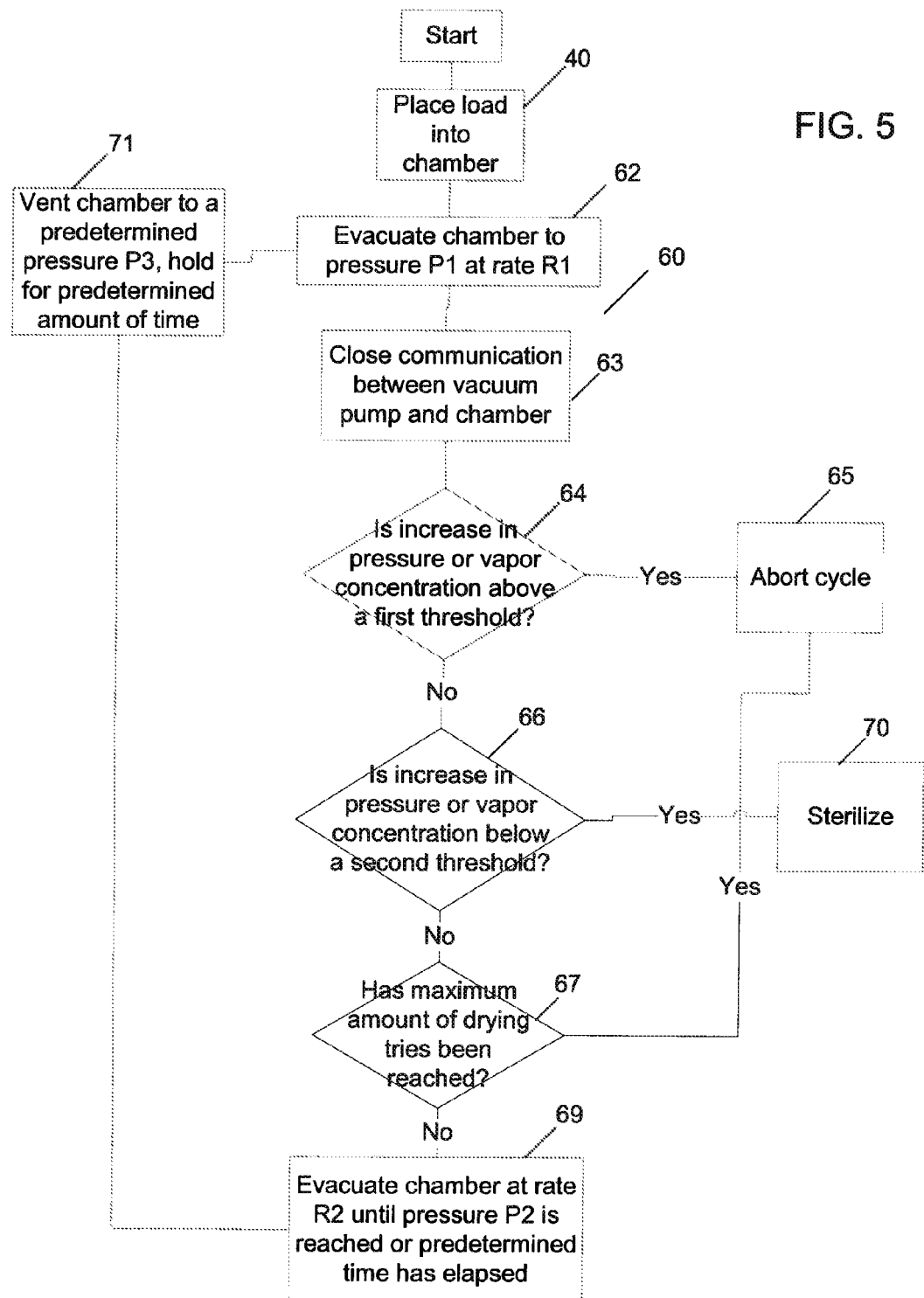
FIG. 5 is a flow chart illustrating still another drying method.

FIG. 5a is a plot of pressure versus time. The dotted line represents a condition in which the load is too wet for efficient drying using the process illustrated in FIG. 5. The solid line shows sufficient drying of the load for sterilization purposes upon completion of two of the drying cycles illustrated in FIG. 5. While FIG. 5a, like FIGS. 2a, 3a and 4a, shows two cycles leading to sufficient drying, the reader should understand that a lesser or greater number of cycles may need to be employed to provide for a sufficiently dry load. The reader should also understand that while FIGS. 2, 3, 4 and 5 all show sterilization the step following sufficient drying, the drying processes described above can be employed for purposes other than preconditioning a load for sterilization. Likewise, various sterilization processes can be employed and can involve a number of steps. Several preferred sterilization processes are discussed below. Others can be employed without deviating from this invention.

Figure 6:
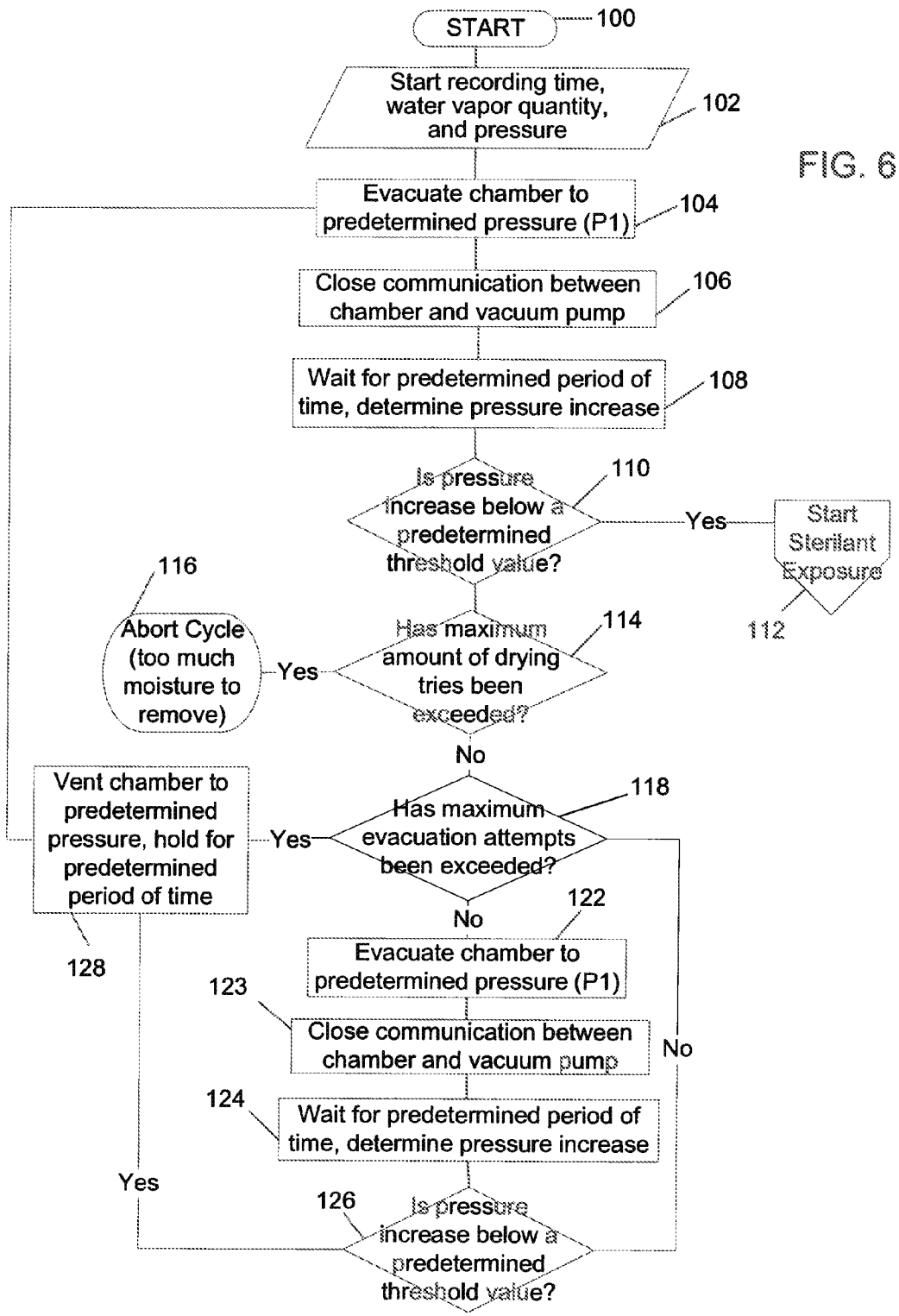
FIG. 6 is a flow chart illustrating another drying method.

FIG. 6 shows still another preconditioning and drying process. At step 100 a load to be sterilized is placed in the sterilization chamber 10 and the sterilization chamber 10 is sealed. At step 102, the controller 32 begins recording time, water vapor concentration and pressure. The controller 32 will typically obtain time information from the internal clock of the controller 32. Water vapor concentration is obtained by the controller 32 from sensor 30 and pressure is obtained by the controller 32 from pressure sensor 26.

At step 104 the chamber 10 is evacuated to a first predetermined pressure P1. This pressure is preferably below the vapor pressure of water at the temperature of the load. Step 104 is carried out by opening valve 14 and operating pump 12.

When the pressure in the chamber 10 reaches P1, the process proceeds to step 106. At step 106, the valve 14 is closed, thus closing fluid communication between the chamber 10 and the pump 12. At step 108, the process includes a built-in delay. During this delay, the controller 10 uses signals from pressure sensor 26 to measure pressure in the chamber 10. Alternatively, the controller 32 uses signals from sensor 30 to measure water concentration in the chamber 10. The controller 10 uses these pressure or water concentration readings to determine any increase in pressure or water concentration within the chamber 10 during the delay or some portion thereof. Since the chamber 10 is sealed and all the valves 14, 18 and 22 are in their closed positions, any increase in pressure or water concentration is likely attributable to evaporation of water from the load.

At step 110, the controller 32 compares the amount of any increase in pressure or water vapor concentration with a predetermined threshold valve. If the increase is below the threshold value, the controller 32 moves to step 112 to initiate sterilization. At the conclusion of any of the drying methods described herein and prior to commencement of the sterilization methods discussed with reference to FIGS. 7 and 8, it may be useful to vent the chamber 10. Specifically, valve 18 may be opened allowing pressure in the chamber 10 to increase to some predetermined pressure such as atmospheric pressure. The valve 18 is then closed and a sterilization cycle is commenced after a suitable time period.

If at step 110 the controller 32 determines the increase in pressure or water concentration is at or below the predetermined threshold, the controller 32 performs step 114 and determines whether a maximum number of drying attempts has been exceeded. If so, step 116 is performed and the cycle is aborted. If not, the controller 32 advances to step 118. At step 114 the controller 32 is specifically comparing the number of times step 104 has been performed to a predetermined maximum.

Steps 118 through 126 provide further drying within a smaller range of operating pressures. Specifically, at step 122 the pressure in chamber 10 (which previously increased due to evaporation of water from the load above pressure P1) is again evacuated to pressure P1 by opening valve 14 and operating pump 12. When pressure P1 is reached, valve 14 is closed at step 123. At step 124, the process provides a built-in delay during which pressure (or water concentration) in the chamber 10 is again measured. At step 126, a check is made to see if the pressure or water concentration increase during step 124 was below a predetermined threshold. If not, the controller repeats step 118 checking to see if a maximum number of evacuation attempts has been exceeded, e.g., whether step 122 has been performed more than a predetermined number of times.

Steps 118, 122, 124 and 126 are repeated until either at step 118 the maximum number of evacuation attempts is determined to have been exceeded or at step 126 the pressure (or concentration) increase is determined to be below the threshold valve. When either of these two events first occurs the controller performs step 128.

At step 128, the chamber is vented to a predetermined pressure which may be, by way of example, atmospheric pressure. This is achieved by opening valve 18 and admitting air into the chamber that may have been heated and/or dried by the heater/drier 19. The chamber 10 is then held at this pressure for a predetermined time, warming the load and replacing energy that may have been removed from the load during the evaporation of water. Once the predetermined time has elapsed, the controller returns to step 104.

From the foregoing, the reader will understand steps 118 and 114 ensure the drying process never gets locked in an unending, repeating cycle. The drying cycle will either end successfully with sterilization being initiated at step 112 or aborted at step 116. What the reader may not fully appreciate is the process shown in FIG. 6 ensures formation of ice in the chamber does not unduly interfere with drying. Maintaining the pressure at a predetermined value less than or equal to P1 is less efficient in terms of time spent to remove water if ice is forming than performing step 128. Steps 118 through 126 ensure significant time is not wasted in the event ice is forming.

Figure 7:
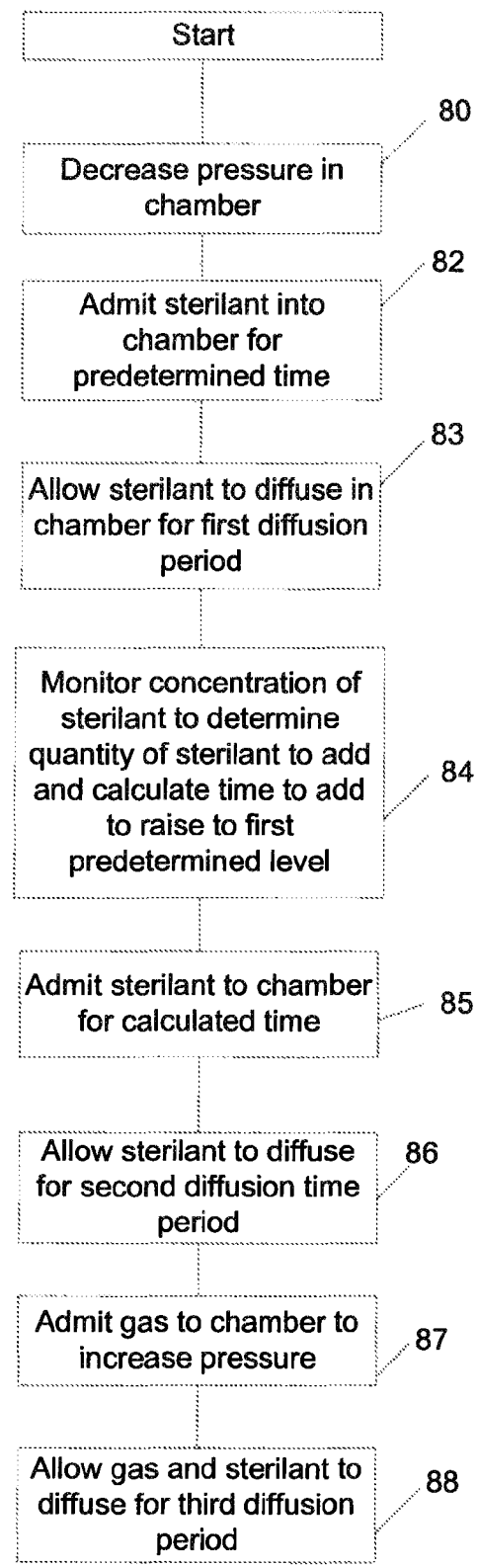
FIG. 7 is a flow chart illustrating a first sterilization cycle.
Figure 8:
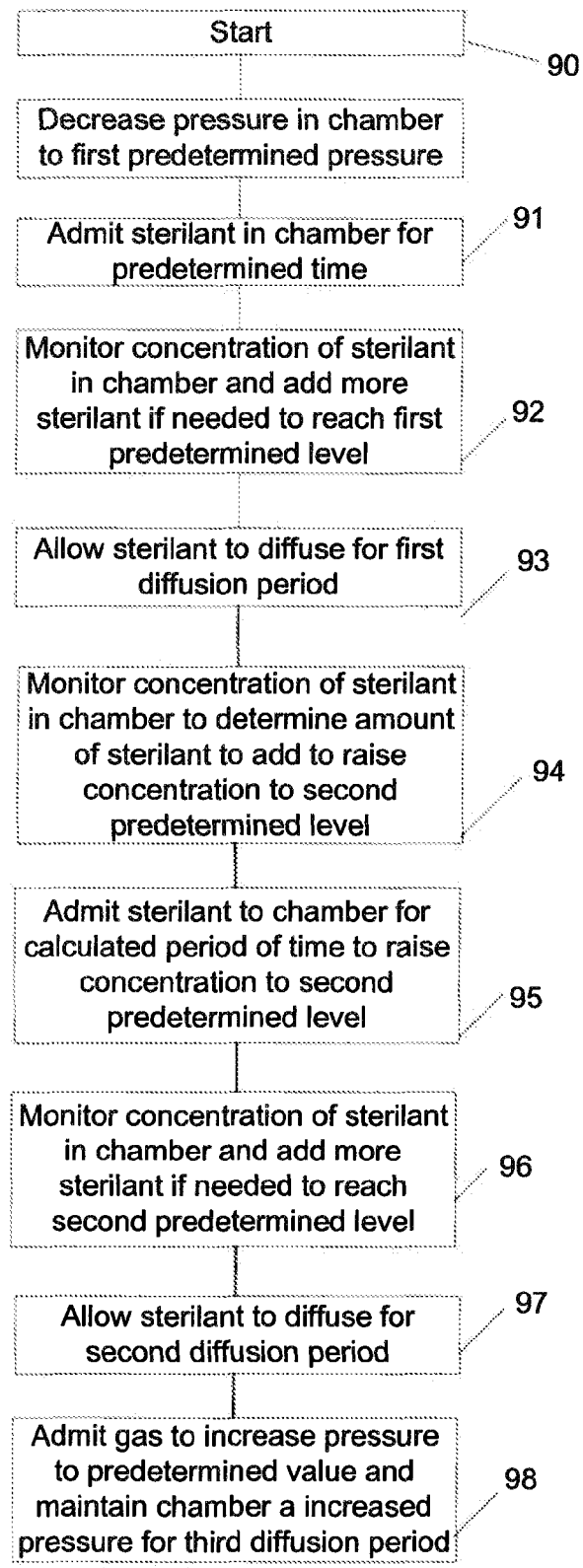
FIG. 8 is a flow chart illustrating a second sterilization cycle.

FIGS. 7 and 8 illustrate two preferred sterilization methods employed using the apparatus of the present invention. While it is preferable to carry out these methods after applying one of the drying methods described above to the load, the reader should recognize that other methods can be used to ensure the load is sufficiently dry for effective and efficient sterilization as a precursor to the sterilization methods illustrated in FIGS. 7 and 8. The sterilization method illustrated in FIG. 7 will now be described.

With the load sealed in the chamber 10 and the valves 18 and 22 closed, the valve 14 is opened and the pump 12 is activated to decrease the pressure in the chamber 10 at step 80 in FIG. 7. Once the pressure in the chamber 10 reaches a suitable level, the valve 14 is closed. Heat can then be optionally applied to the load if deemed desirable. The pressure in the chamber at this point will generally be below 1 Torr, preferably below 200 mTorr, and most preferably as low as possible.

At step 82, another valve 22 is opened to permit sterilant to flow from the sterilant source 20 into the chamber 10 for a predetermined time. If the contents of the sterilant source 20 are, for example, an aqueous solution of hydrogen peroxide, the solution is vaporized by vaporizer 21 so that only hydrogen peroxide vapor and water vapor enter chamber 10. As noted elsewhere, sterilants other than hydrogen peroxide can be used and the sterilant can be stored in a gaseous or vaporous form, thus eliminating the need for the vaporizer 21 without deviating from the invention. Likewise, when non-aqueous forms of hydrogen peroxide are used, the vaporizer 21 can be eliminated. After a predetermined time period, the valve 22 is closed to complete step 82.

At step 83, the sterilant is allowed to diffuse throughout the chamber 10 for a first diffusion period. The duration of this diffusion period is preferably between 5 and 60 seconds. Either during or after completion of this first diffusion period, the concentration of sterilant admitted into the chamber 10 during step 82 is assessed as indicated at step 84. Preferably, the controller 32 uses signals received from a sensor 28 related to the concentration of the sterilant within the chamber to determine the amount of time the valve 22 should be opened to raise the concentration of sterilant in the chamber 10 to a first predetermined level. This time period will vary based on the size, condition, and content of the load being sterilized in the chamber 10. This determination involves a calculation of the quantity of sterilant required to reach the first predetermined level and then a calculation of the time the valve 22 needs to be opened to admit enough sterilant into the chamber 10 to achieve the first predetermined concentration level. This first predetermined concentration level is preferably between 3 and 17 mg/L.

At step 85, valve 22 is opened to admit additional sterilant into the chamber 10 and then the valve 22 is closed at the conclusion of the time interval calculated during step 84. At step 86, the gas is allowed to diffuse for a second time period preferably lasting between 5 and 60 seconds.

At step 87, which follows the conclusion of the second diffusion time period, a valve 18 is opened to admit air, or another gas, into the chamber from the gas source 16. The valve 18 is closed either after a predetermined time period or when the pressure sensor 2'6 sends a signal to the controller 32 indicating the pressure within chamber 10 either has reached atmospheric pressure or some other selected subatmospheric pressure. At step 88, the mixture including sterilant vapor (and water vapor) admitted in steps 82 and 85 and the gas admitted in step 87 are allowed to diffuse within the chamber 10 for a third diffusion period to complete the sterilization process. The third diffusion period preferably has a duration of 0 to 5 seconds.

While removing the load from the chamber 10 could immediately follow the sterilization process depicted in FIG. 7, the residual concentration of sterilant in the chamber 10 and on the surfaces of the load may be too high for safe removal. Several options are available to address this depending on the sterilant used and the time constraints then existing. For example, the user could simply leave the chamber 10 sealed until the sterilant decomposes to an acceptable level. Alternatively, the controller 32 could evacuate the chamber 10 and then activate a gas plasma generator 24. Also, the residual sterilant can be exhausted from the chamber 10 by opening valve 14 and running the pump 12. At the same time, a valve 18 can be opened so as to create a flow of air or other gas through the chamber 10. Alternatively, the valves 18 and 14 along with the pump 12 can be actuated by the controller 32 to repeatedly evacuate and vent the chamber 10 until an acceptable residual level of sterilant is reached. Combinations of these techniques can also be employed.

FIG. 8 illustrates a more refined sterilization process based upon the same principles as the process illustrated in FIG. 7. With the load sealed in the chamber 10 and sufficiently dry for efficient sterilization the pressure in the chamber 10 is decreased to a first predetermined pressure at step 90. Ideally, this first predetermined pressure is in the range of 0-1 Torr. Drawing the chamber 10 down to this pressure is achieved by keeping the valves 18 and 22 closed while the valve 14 is open and the pump 12 is operating. When the first predetermined pressure is reached, the valve 14 is closed.

At step 91, valve 22 is opened for a predetermined period of time to allow sterilant to flow from the sterilant source 25 through the vaporizer 21 and into the chamber 10. As noted above, the vaporizer 21 may not be necessary if, for example, non-aqueous sterilants are used. The valve 22 is closed at the end of this predetermined time period.

Step 92 provides a check to ensure that the concentration of sterilant in the chamber 10 is at a first predetermined level. Specifically, signals representative of the sterilant concentration level are sent to the controller 32 by the sterilant concentration sensor 28. If the controller 32 determines the sterilant concentration is below the first predetermined level, the controller 32 calculates how much sterilant must be added to reach the first predetermined level, how long the valve 22 must be in the open position to admit that quantity of sterilant and then opens the valve 22 for the calculated time period. The substeps of checking, calculating and admitting sterilant can be repeated until the concentration of sterilant within the chamber 10 reaches the first predetermined level. This first predetermined level is preferably in the range of 0.5 to 1.5 mg per liter.

At step 93, and with the concentration of sterilant at the first predetermined level, the sterilant is allowed to diffuse for a first diffusion period. This first diffusion period will preferably have a duration of 0 to 5 minutes. Sterilants such as hydrogen peroxide tend to break down over time. If such sterilants are employed, valve 22 can be opened for a predetermined period of time long enough to increase the sterilization concentration in the chamber above the first predetermined level when performing step 92. Once enough time has elapsed for the sterilant to vaporize (such as when the sterilant is an aqueous solution) and diffused through the chamber, valve 14 can be opened to reduce the concentration of sterilant to the first predetermined level. Once the sterilant concentration returns to this first predetermined level, valve 14 is closed. Step 94 can be carried out either during or immediately after the first diffusion period. In carrying out step 94, the controller 32 monitors the signals generated by sterilant concentration sensor 28 and uses these signals to determine the amount of sterilant required to raise the sterilant concentration to a second predetermined level and how long the valve 22 should be opened to raise the sterilant concentration in the chamber 10 to that level. This second predetermined sterilant concentration level is preferably in the range of 1.5 mg per liter to a maximum possible level of concentration before condensation is detected in chamber 10. At step 95, the valve 22 is opened by the controller 32 for the period of time calculated in step 94 and then closed.

Step 96 is similar to step 92. In step 96, the controller 32 uses signals from the sensors (e.g., sensor 28) to determine whether the sterilant concentration in the chamber 10 has reached the second predetermined level. If not, the controller 32 calculates the quantity of sterilant that must be added and the period of time the valve 22 should be opened to admit that quantity of sterilant. The controller 32 then opens the valve 22 for the calculated time period. The various substeps of step 96 can be repeated until the second predetermined concentration level is reached.

After the sterilant concentration has reached the second predetermined level, the sterilant is allowed to diffuse for a second diffusion period at step 97. This second diffusion period is preferably between 0 and 10 minutes in duration. At step 98, following the second diffusion period, the controller 32 opens the valve 18 to increase the pressure to a predetermined value. The value is selected to cause sterilant to move into lumens and other small spaces without undue dilution of the sterilant. The controller 32 monitors signals from the pressure sensor 26 and closes the valve 18 when the pressure within the chamber 10 reaches this predetermined value and the pressure is maintained at that predetermined value for a third diffusion period to complete the sterilization process. At the conclusion of the sterilization process, residual concentrations of sterilant can be addressed as described above.

One advantage of the sterilization method described above is the atmosphere driven into the load when the sterilant concentration is increased to the second predetermined level at step 94 has been consistently conditioned with sterilant during steps 91-93. Whenever the pressure in the chamber is increased (e.g., by adding sterilant or by venting), a pressure differential is created between the chamber and the load, which causes the atmosphere existing within the chamber to be driven into the load. When a stable sterilant is employed, the sterilant added to reach the first predetermined level is driven into the load when the concentration is increased to the second predetermined level. If a sterilant tending to break down over time is employed, these benefits are enhanced by increasing the concentration above the first predetermined level and then reducing the concentration to the first predetermined level to consistently condition the atmosphere prior to performing step 94 and increasing the concentration to the second predetermined level.

From the foregoing, those skilled in the art will recognize many advantages afforded by the present invention. The present invention is not limited to the specific embodiments described above. Those skilled in the art will recognize variations to the apparatus and the processes described can be made without deviating from the invention.

What is claimed:

1. A method of removing moisture from a load to be sterilized in a chamber comprising:
   (a) placing the load in the chamber;
   (b) reducing the pressure within the chamber at a first rate to a first predetermined subatmospheric pressure below the vapor pressure of water at the temperature of the load;

(c) monitoring over a predetermined period of time the increase in the quantity of vapor within the chamber resulting from evaporation of moisture from the load;
(d) comparing the increase in quantity of vapor within the chamber to a first upper threshold and a second lower threshold, proceeding to step (e) to perform further drying in response to the increased quantity of vapor is between the first upper threshold and the second lower threshold;
(e) reducing the pressure within the chamber at a second slower rate slow enough to prevent ice from forming in the chamber while monitoring changes in the quantity of vapor within the chamber;
(f) admitting warm, dry gas into the chamber;
(g) repeating steps (b)-(f) to remove moisture until the increased quantity of vapor is below the second lower threshold; and
(h) applying a sterilant to the load in the chamber.

2. The method of claim 1 wherein step (g) is performed a predetermined number of times.

3. The method of claim 1 wherein step (g) is performed continuously for a predetermined period of time.

4. The method of claim 1 wherein steps (e), (f) and (g) cease to be performed once the increase in the quantity of vapor within the chamber during said predetermined time period does not exceed the second lower threshold.

5. The method of claim 1 wherein the increase in the quantity of vapor within the chamber is monitored using a pressure sensor.

6. The method of claim 1 wherein the increase in the quantity of vapor within the chamber is monitored using a sensor comprising a light source directing light, of a known intensity and of a wavelength likely to be absorbed in part by the vapor, through at least a portion of the chamber to a detector measuring the intensity of unabsorbed light reaching the detector.

7. The method of claim 1 wherein the gas is at least at a first predefined temperature when admitted into the chamber.

8. The method of claim 1 wherein the gas has a water vapor concentration below a predefined level before the gas is admitted into the chamber.

9. The method of claim 1 wherein the gas admitted into the chamber enhances evaporation of moisture from the load.

10. The method of claim 9 wherein the gas admitted into the chamber enhances evaporation of moisture from the load by enhancing heat transfer to the load.

11. A method for removing moisture from a load to be sterilized in a chamber coupled to a vapor sensor, an evacuation pump and a source of gas, the method comprising:
(a) placing the load in the chamber;
(b) operating the evacuation pump to decrease at a first rate the pressure within the chamber down to at least a first predetermined pressure that is subatmospheric and below the vapor pressure of water at the temperature of the load to cause evaporation of moisture from the load;
(c) monitoring over a predetermined period of time increases in the quantity of vapor in the chamber resulting from said evaporation of moisture from the load;
(d) comparing the increase in the quantity of vapor in the chamber to a first threshold and a second lower threshold and proceeding to step (e) in response to the increased quantity of vapor is between the first threshold and the second lower threshold;
(e) reducing the pressure within the chamber down to at least a second predetermined pressure to cause additional evaporation of moisture from the load, but at a second slower rate slow enough to prevent ice from forming in the chamber;
(f) admitting warm, dry gas into the chamber to enhance heat transfer to the load and raise the pressure within the chamber;
(g) repeating steps (b)-(f) to further dry the load until the increased quantity of vapor is below the second lower threshold; and
(h) subjecting the load in the chamber to a sterilant.

* * * * *